United States Patent [19]

Bates et al.

[11] Patent Number: 5,658,296
[45] Date of Patent: Aug. 19, 1997

[54] METHOD FOR MAKING SURGICAL RETRIEVAL BASKETS

[75] Inventors: James S. Bates, Bloomington; Craig R. Kline, Spencer; James W. Riley, Bloomington; Tony E. Weber, Plainfield; Gary D. Wood, Spencer, all of Ind.

[73] Assignee: Boston Scientific Corporation, Natick, Mass.

[21] Appl. No.: 342,911

[22] Filed: Nov. 21, 1994

[51] Int. Cl.⁶ ............................................. A61B 17/22
[52] U.S. Cl. ............................................. 606/127; 128/898
[58] Field of Search .................................. 606/113, 114, 606/127; 128/898

[56] References Cited

U.S. PATENT DOCUMENTS

| | | |
|---|---|---|
| 1,677,671 | 7/1928 | Councill . |
| 3,108,593 | 10/1963 | Glassman . |
| 3,137,298 | 6/1964 | Glassman . |
| 3,472,230 | 10/1969 | Fogarty . |
| 3,791,387 | 2/1974 | Itoh . |
| 4,046,150 | 9/1977 | Schwartz et al. . |
| 4,198,960 | 4/1980 | Utsugi . |
| 4,299,225 | 11/1981 | Glassman . |
| 4,347,846 | 9/1982 | Dormia . |
| 4,557,255 | 12/1985 | Goodman . |
| 4,590,938 | 5/1986 | Segura et al. . |
| 4,611,594 | 9/1986 | Grayhack et al. . |
| 4,612,931 | 9/1986 | Dormia . |
| 4,633,871 | 1/1987 | Shinozuka . |
| 4,741,335 | 5/1988 | Okada . |
| 4,790,812 | 12/1988 | Hawkins, Jr. et al. . |
| 4,881,530 | 11/1989 | Thoma et al. ............... 148/11.5 R |
| 4,927,426 | 5/1990 | Dretler . |
| 4,997,435 | 3/1991 | Demeter . |
| 5,057,114 | 10/1991 | Wittich et al. . |
| 5,059,205 | 10/1991 | El-Nounou et al. . |
| 5,064,428 | 11/1991 | Cope et al. . |
| 5,074,867 | 12/1991 | Wilk . |
| 5,176,688 | 1/1993 | Narayan et al. . |
| 5,190,542 | 3/1993 | Nakao et al. . |
| 5,190,557 | 3/1993 | Borodulin et al. . |

*Primary Examiner*—Robert A. Hafer
*Assistant Examiner*—Benjamin K. Koo
*Attorney, Agent, or Firm*—Pearson & Pearson

[57] ABSTRACT

A method for forming a surgical retrieval basket includes cold forming a section of each of a plurality of axially extending wires in a predetermined shape. Securing the wires together proximate the sections with a cavity defined between the sections of the plurality of the wires forms an enlarged portion of a surgical retrieval basket. The retrieval basket comprises a plurality of wires normally encased in a compact form within a sheath whereupon displacement of the sheath to free a portion of the wires enables the wires to form an enlarged retrieval basket. The wires forming the retrieval basket are cold formed in a predetermined shape and are secured together in a predetermined fashion to define the retrieval basket.

27 Claims, 3 Drawing Sheets

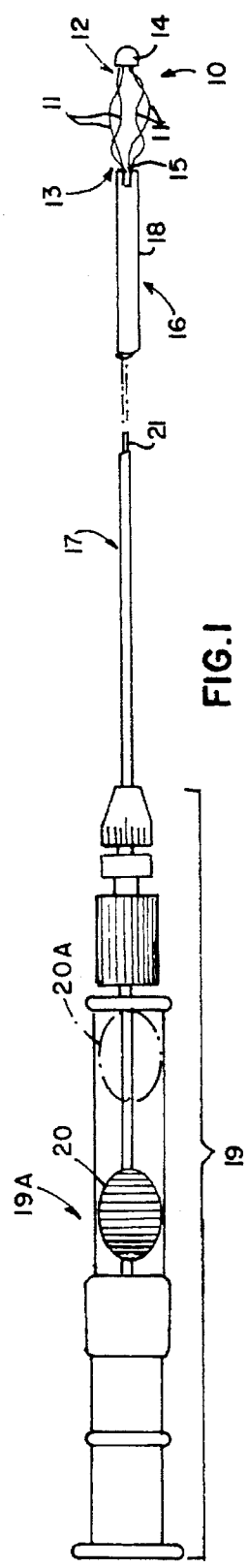
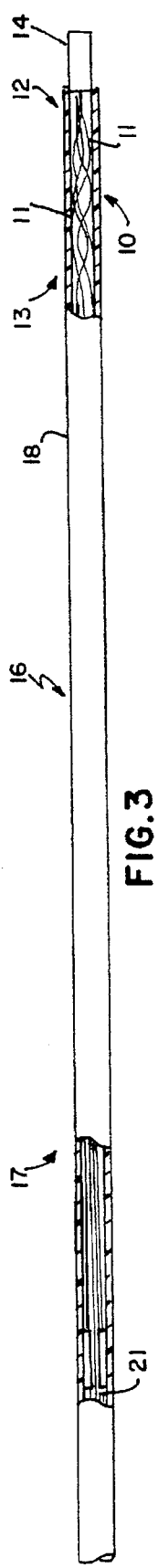
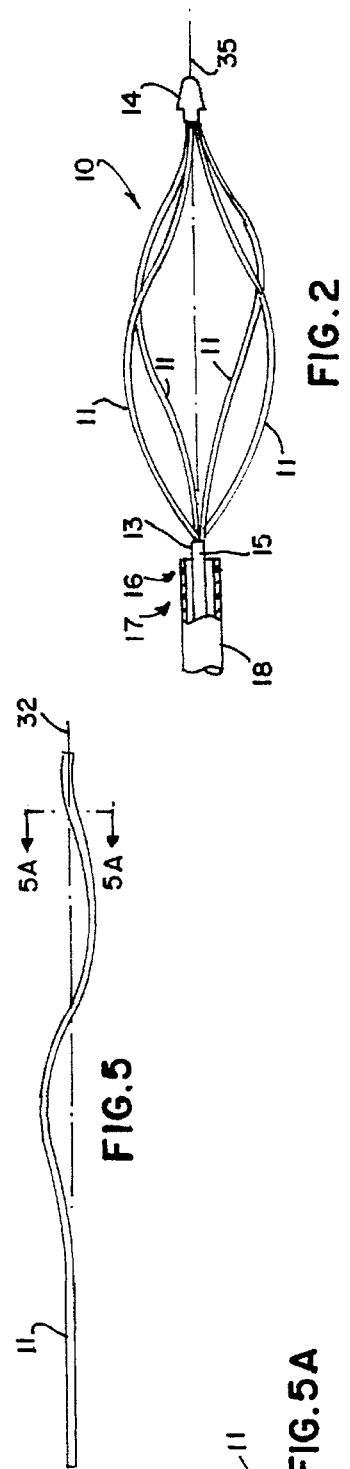
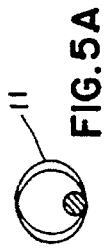

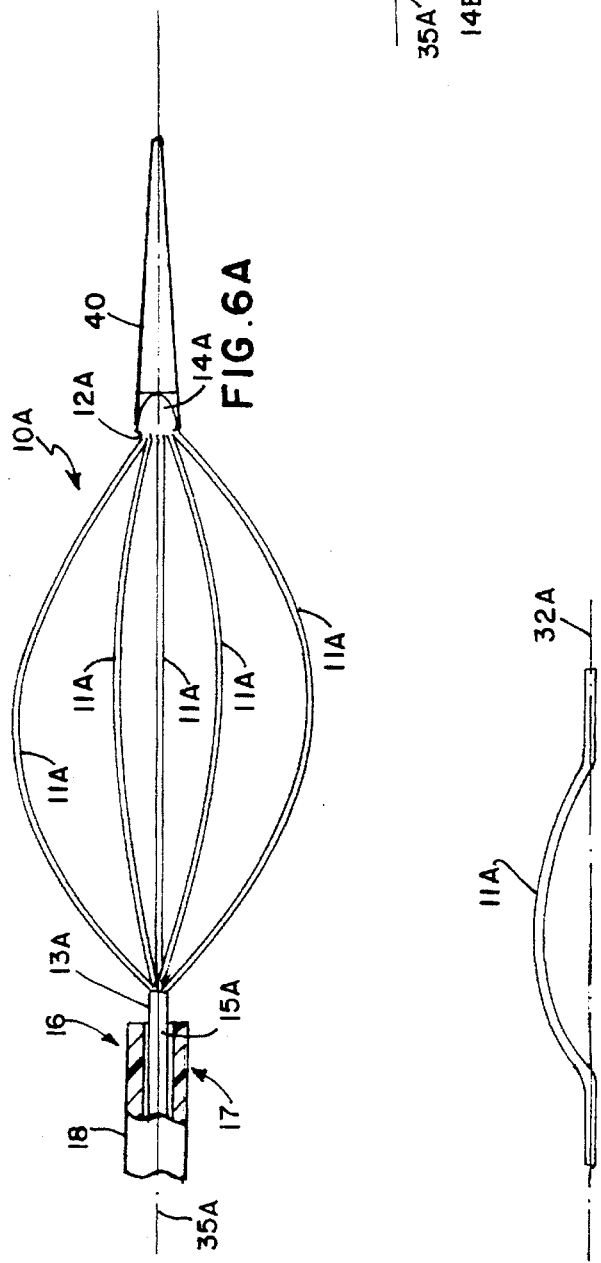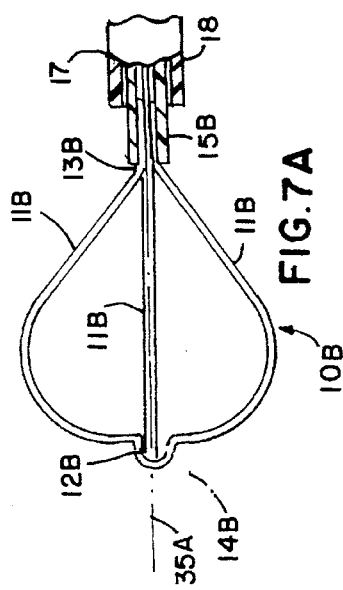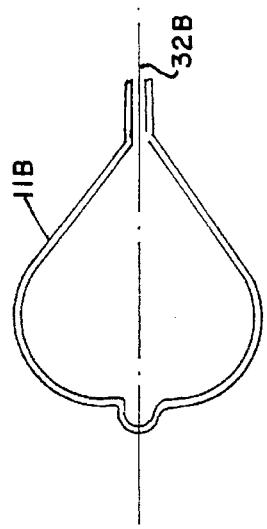

METHOD FOR MAKING SURGICAL RETRIEVAL BASKETS

BACKGROUND OF THE INVENTION

1. Field of the Invention

This invention generally relates to medical instruments and more specifically to surgical retrieval baskets for removing an object from a body, particularly calculi that can form in the biliary and urinary systems, and a method for making such surgical retrieval baskets.

2. Description of Related Art

Recently developed medical instruments reduce the invasiveness and potential trauma previously associated with various medical procedures. The removal of calculi in the form of kidney stones, gallstones and the like from the body is one area where this effort is meeting with success. Various instruments now permit the removal of kidney stones and gallstones without the need for major surgery.

Some of these instruments incorporate miniaturized grasping forceps. Others incorporate a mechanical retrieval basket as described in the following U.S. Pat. Nos.

4,590,938 (1986) Segura et al
4,611,594 (1986) Grayhack et al
4,625,726 (1986) Duthoy
4,807,626 (1989) McGirr
5,064,428 (1991) Cope et al.
Ser. No. 08/258,121 (1994) Bates et al.

The Segura et al. patent discloses a surgical extraction device that can be inserted through the working channel of an endoscope for removing stones and the like from the kidneys or the ureter or biliary duct. The device includes a retrieval basket of relatively large diameter that is extendable from the distal end of a sheath and collapsible when withdrawn into the sheath. Outwardly bowed flat wire spring strips form the retrieval basket. These strips extend generally axially of the sheath and join at respective distal and proximal ends. The retrieval basket has a generally bulbous form that is relatively stiff due to the spring strip construction and that facilitates dislodgment and capture of stones.

The Grayhack et al. patent discloses another retrieval basket that is useful during the removal and/or destruction of calculi. A smooth outer tubular sheath encases a stranded helical wire cable terminating in a protective tip at the working or distal end of the device. When the cable is extended distally, the spring wire strands at the working end of the cable expand to form a retrieval basket. The distal end of this device additionally includes an expandable distal portion for protecting surrounding tissue during withdrawal of the device and calculi.

The Duthoy patent discloses an extraction device that includes a retrieval basket formed from a plurality of wires spaced about and outwardly from an imaginary extension of the center line of a hollow cable. A filiform extends distally from the distal end of the retrieval basket to extend past a stone and to allow the basket to be threaded around and onto the calculi.

The McGirr patent discloses an extractor included a self-closing retrieval basket at the distal end of a catheter with a flexible control line for opening the basket from the proximal end of the catheter. The basket assumes a normal position wherein it is in a compact closed form. Pulling on the control line flexes the strips to open the basket. When the control line is released, the strips relax and surround the calculi or object being removed.

The Cope et al. patent discloses a stone retrieval basket having superelastic individual wire loops secured together at the apex of the loops to define a distal end of a basket which can be insert through and beyond a distal end of an elongated tube. Sleeves which secure the wires in a spaced relation defines the proximal end of the basket so as to define a basket having a bulbous shape.

The Bates et al. patent application, that is a co-pending application commonly assigned with this application, discloses a surgical retrieval basket comprising axially extending wires that are grouped in sets of filaments. The wires are normally maintained in an overlying sheath in a compact condition and form an enlarged basket upon retraction of the sheath. The filaments of a set are relatively closely angularly spaced with the sets being relatively widely spaced to provide a greater number of contact points with entrapped calculi without significantly increasing the manipulations necessary to capture such calculi in the basket.

These and other surgical extractors using retrieval baskets have certain common characteristics. Each retrieval basket comprises a plurality of strands in the form of individual helical or flat wires substantially equiangularly spaced about the retrieval basket which is collapsible into a compact form. In some retrieval baskets the strands are formed along substantially straight lines when the basket is in the compact form (i.e., so-called "flat wire baskets"); in others, the individual strands extend along a generally helical path (i.e., so-called "helical wire baskets). Each instrument generally include a plurality of three or more strands, with the flat wire basket comprising an even number due to manufacturing constraints, as explained below.

Forming such wire baskets generally comprises grouping a plurality of axially extending wires having shape memory properties, such as stainless steel, to extend along parallel axes. Securing to wires together defines a basket subassembly having a distal and proximal end between which each of the wires extend. An operator uses a forming fixture, generally hand operated, and cold-works the wires of the subassembly to define the shape and form of the basket as either a helical wire or straight wire basket.

To form a straight wire type basket the forming fixture generally receives and secures distal and proximal ends on a straight wire axis. Generally, the forming fixture includes a mount fixing one of the ends along the axis and another mount biased so that the other end can move along the axis toward the one end during the forming process. A forming tool, generally comprising a linearly extending member corresponding to the desired radial extension of the basket to be formed, engages an opposed pair of the wires mediate the ends of the wires to urge the wires radially outward from the wire axis defined between the ends of the subassembly. Specifically, the tool rotates (e.g., +75° to −75°) on transverse axes so that the opposed ends of the tool slide along the engaged wires and prestresses the wires into the desired form. Repetition of this for other wire pairs defines a straight wire basket having an even number of wires with each wire extending in a substantially single plane with respect to the basket axis and in an arc-like fashion between the distal and proximal ends of the basket. This technique thus limits a straight wire retrieval basket to an even number of wires, because it operates on opposed wires in a pair simultaneously.

Alternatively, as described by Segura et al. a hand operated forming fixture acts on individual wires and includes a plurality of upwardly extending pins. The tool bends (i.e., cold works) each wire about the pins to form them in a desired loop shape. The ends of each of a plurality of individual wires, thus formed, are then secured together to define a proximal end of the straight wire retrieval basket. Since each wire comprises a first portion extending from the proximal to a distal end of the basket and a second portion extending from the distal to proximal end, straight wire baskets formed by this method also essentially comprise an even number of wires extending from the proximal to a distal end of the straight wire basket.

In forming a helical wire basket the desired number numbers of wires also are grouped together and secured at their ends along a wire axis. The ends of the subassembly are also fixed in a forming fixture. However, in this case opposed tools usually secure the wires in a generally equiangular spaced arrangement radially extended from the axis. Turning the tools about the axis in opposed senses (i.e., one is turned clockwise and the other is turned counterclockwise) bends and stresses the wires to provide their helical, radially extending path between the ends of the basket.

These processes for forming retrieval baskets thus generally comprise the selection of wires, formation of a wire sub-assembly, and the cold working of the wires. Each method is labor intensive, as the forming fixtures of the prior art are hand operated. Significant tooling expenses are incurred as each basket size and shape generally requires its own separate tools. Further, differences between individual tools and fixtures and the processes used by individual operators leads to variations between wires of a basket and between baskets produced thereby. That is, the baskets tend to be inconsistent in their properties and characteristics. Additionally, cold-working introduces significant stress in the wires that can affect their characteristics such that individual wires have different characteristics even within one retrieval basket. Such inconsistencies often cause additional inconvenience in the use of retrieval baskets and can result in additional trauma to a patient. For example, inconsistencies in the spacing of wires can render capture and retention of objects more difficult while over stressed and/or fatigued wires can lead to premature wire failure and more fragile baskets. Frequently upon the failure of a wire in a retrieval basket, the wires tend to curl up into a ball like arrangement. The lose ends of the broken wire can injure body tissue and the ball formed by the curling up of the wires may also require major surgery to enable removal of the retrieval basket from the body.

Thus, the prior art methods fail to provide adequate controls over the forming of the wires and, thus, the basket. These methods generally do not include heat treating the wires once formed, because such heat treatment would tend to destroy the securement of the wires at the distal and proximal ends of the retrieval basket.

SUMMARY

Therefore it is an object of this invention to provide a repeatable method for producing wire retrieval baskets with consistent characteristics.

It is another object of this invention to provide a method for making wire retrieval baskets that comprise wires of a preformed shape.

It is yet another object to provide a method for making wire retrieval baskets that is relatively inexpensive and simple.

It is a still further object of this invention to provide a method for making wire retrieval baskets that assembles cold formed wires having desired tensile strength, ductility, dilation force, and spring memory characteristic to form such baskets.

According to one aspect of this invention a method for forming a surgical retrieval basket includes cold forming a plurality of axially extending wires in a predetermined shape to extend radially from the axis along a portion of the wires between opposed ends of each of the wires. Securing the cold formed wires together at opposed ends of the portions with a cavity defined between the portions forms an enlarged portion of a retrieval basket.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of a surgical extractor constructed in accordance with this invention with a handle at a proximal end and an expanded retrieval basket at a distal end;

FIG. 2 is a enlarged plan view of the distal end of the extractor shown in FIG. 1;

FIG. 3 is an enlarged view, partially in cross section, of the distal end of the extractor shown in FIGS. 1 and 2 in a compact form;

FIG. 5 is a plan view of a helically wound wire of the retrieval basket of the surgical extractor of FIG. 1;

FIG. 5A is a cross-sectional view of the wire of FIG. 5 taken along lines 5A—5A;

FIG. 6A depicts the distal end of a surgical extractor incorporating a different embodiment of a retrieval basket according to this invention;

FIG. 6B is a plan view of a wire of the retrieval basket of the surgical extractor of FIG. 6A;

FIG. 7A depicts the distal end of another surgical extractor with still a different retrieval basket according to this invention; and FIG. 7B is a plan view of a wire of the retrieval basket of the surgical extractor of FIG. 7A.

DESCRIPTION OF ILLUSTRATIVE EMBODIMENTS

Figure 4:
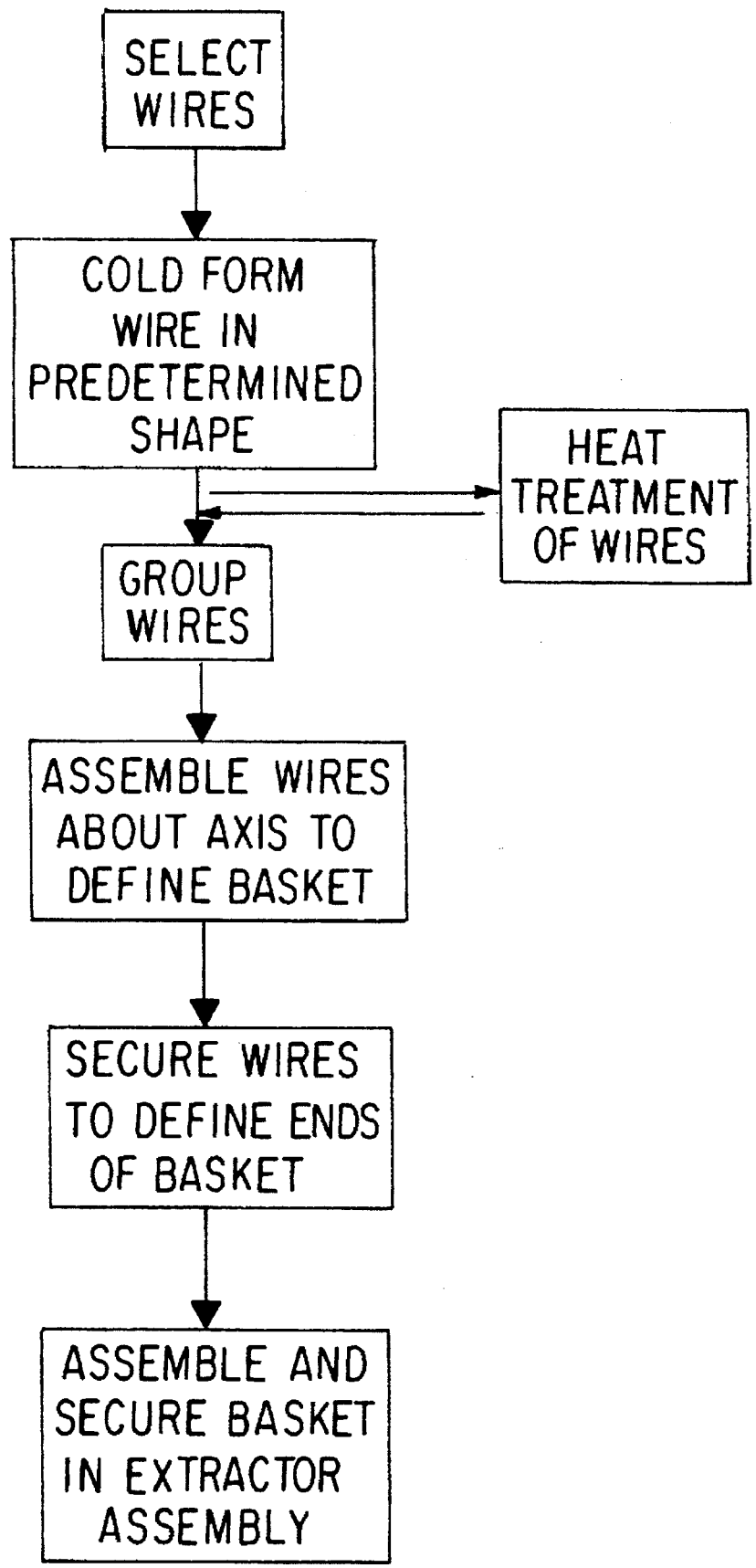
FIG. 4 is a diagram that describes the steps for forming a surgical extractor in accordance with this invention.

FIGS. 1 through 3 depicts a wire retrieval basket 10 formed according to the present invention. Specifically, the retrieval basket 10 comprises a plurality of wires 11 which extend along a generally helical path from a distal end 12 to a proximal end 13 of the basket 10. Each of the wires 11 is substantially equiangularly spaced relative to adjacent ones of the wires 11 and constitutes a turn in the helix. A cap 14 secures the wires together at the distal end 12 by solder, swaging or other known technique. A sleeve 15 similarly secures the wires 11 together at the proximal end 13.

The basket 10 typically is part of a distal end 16 of an extractor 17 which a physician introduces into a patient in the form shown in FIG. 3. In this form a sheath 18 retains the basket in a compact form until the extractor 17 is positioned proximate to calculi to be retrieved. The physician holding the base portion 19 of a handle 19A moves a slider 20 captured in the base portion 19 and connected to the sheath 18 from the position 20A depicted in phantom in FIG. 1 to the position 20. This displaces the sheath 18 and the wires 11 return to their original shape as shown in FIG.

2 thereby to dilate surrounding tissue and to provide a structure that can be manipulated over the calculi.

The physician then manipulates the retrieval basket 10 via a proximally extending control cable 21 connected to the wires 11 and captures calculi in the retrieval basket 10. Thereafter the sheath 18 advances distally and reduces the volume of the retrieval basket 10 until it contacts the entrapped calculi so the physician can withdraw the extractor 17 with the entrapped calculi.

Referring now to FIG. 4, the process for forming the retrieval basket 10 in FIG. 1 commences with step 30 that includes the selection of a plurality of wires having substantially the same characteristics. In the context of this invention, wires have the same characteristics, if they are produced by the same techniques and not subject to divergent treatments. Typically, the wires 11 will comprise a suitable shape memory material, such as stainless steel. A cold forming process step 31, such as by stamp pressing, spring forming or other known suitable processes that imparts on a relatively consistent and repeatable basis a desired change in the shape of a section of the individual wires 11. In this instance the forming step provides a plurality of individual wires 11, like those of FIG. 5 and 5A, with a distal section that radially extends in a helically wound fashion from an axis 32 with each of the wires 11 having substantially the same size, shape and characteristics. That is, each of the formed wires 11 exhibit substantially the same physical characteristics and properties so that the internal stress, ductility, tensile strength, and spring memory are relatively constant from wire to wire. Machine processing provides this consistency.

The process of FIG. 4 may also include a heat treating step 33 depending on the materials of the wires. Heat treating can further improve control over the characteristics of certain wires formed of such material as stainless steel. That is, such heat treatments could relieve any internal stress imparted by the cold forming of the wires 11, if needed.

Once the wires 11 are formed in the desired shape with the desired characteristics by steps 31 and 33, they are then grouped and assembled to define a basket shape at step 34. As depicted in FIG. 2, arranging a plurality of the wires 11 about an axis 35 defines a basket shape. Securing the wires at distal and proximal ends 12 and 13 then fixes the wires in their respective positions to form the retrieval basket 10.

Such retrieval baskets, due to the consistency of the wire characteristics and the arrangement of the wires defining the basket, exert a consistent dilation force and expand to a consistent shape. The retrieval basket 10 can then be incorporated in an extractor mechanism such as the extractor 17 of FIG. 1 as indicated by step 36 of FIG. 4 to provide an instrument for retrieving objects from the body of a patient.

From the foregoing description it should now be appreciated that retrieval baskets constructed in accordance with the present invention can comprise a variety of user desired shapes, numbers of wires, and wire spacing. That is the wires can be preformed into predetermined shapes and sizes for assembly in a selected manner to define baskets of a predetermined shape comprising a desired number of wires with a selected spacing between such wires.

The foregoing method of FIG. 4 can also be applied to the formation of retrieval baskets generally, such as straight wire retrieval basket embodiments of this invention depicted as retrieval baskets 10A and 10B of FIGS. 6A, 6B, 7A and 7B, respectively. In the embodiment of FIG. 6A and 6B, each of wires 11A of the retrieval basket 10A of FIG. 6A includes a cold formed distal section (i.e., formed by the step 31 of FIG. 4) that extends radially from a longitudinal axis 32A of such wire 11A as depicted in FIG. 6A. Preferably each of the wires 11A have a rectangular cross-section, but are not helically wound in the distal section. Rather, the radially extended portions in the distal section extend in a substantially co-planar fashion.

The wires 11A are then arranged and secured together about an axis 35A in a known manner to define the basket. In this case, the sleeve 15 secures the wires 11A defining the proximal end 13A of the basket 10A and a cap 14A secures the distal end of the wires 11A to define the distal end 12A of the basket. As with the embodiment of FIG. 2, the wires can, if desired, be heat treated prior to securement to further relieve and define the characteristics of the wires 11A. The particular embodiment depicted in FIG. 6A also includes a filiform 40 carried on the cap 14A that extends distally from the retrieval basket 10A. Such filiforms are know in the art and can be included as an element in any embodiment of this invention.

In the particular embodiment of FIG. 6A, an odd number of the wires 11A (i.e., five) form the basket 10A. Straight wire baskets having cold worked wires of the prior art necessarily included even numbers of wires extending between the proximal and distal ends of the retrieval basket due to the techniques by which the wires forming the baskets shaped. That is, such baskets were formed by loops so that a first portion extended from the proximal to distal ends and a second portion extended from the distal to proximal ends (i.e., a loop) or by opposed pairs of wires, as described above. Those skilled in the art will now recognize that, by constructing the baskets with cold formed or otherwise preformed wires, straight wire baskets having 3, 5 and even more wires comprising an odd number can be readily constructed, as well as, of course such basket having an even number.

It will also be recognized that straight wire baskets constructed in accordance with this invention may have various shapes. For example, baskets with the bulbous distal portion of the retrieval basket 10B of FIG. 7A can also be provided using preformed axially extending wires. Alternatively, the retrieval basket 10B of FIG. 7A can be formed by joining wires preformed by this invention with loops. Specifically, with reference to FIG. 7A, wires 11B define a basket 10B according to this invention with the wires 11B preferably comprising stainless steel strips having a rectangular cross-section. The wires of this basket, unlike the wires of the other baskets 10 and 10A of FIGS. 2 and 6A, do not extend in a generally axial direction. As depicted in FIG. 7B each of the wires 11B form a loop centered about an axis 32B with the ends of the wires 11B extending in the same direction along the axis 32B. Joining a plurality of the preformed wires 11B proximate the base of the loops defines the basket 10B with a distal end 12B defined by the distal intersection of the loops.

The process and baskets formed by joining preformed looped wires like those depicted in FIG. 7A are within the scope of this invention. That is, the wires 11B can be formed prior to the assembly of the basket 10B by automated machinery such as spring forming machinery to produce wires of the appropriate shape according to step 31 of FIG. 4. Such wires can then, if desired, be heated treated according to the step 33 of FIG. 4. Securing the ends of a plurality of wires in a sleeve 15B or by other suitable securing means assembles (step 34) and defines a retrieval basket according to the present invention. A cap 14B can also be suitably secured to the distal end 12B of the basket to provide a limit to the distal travel of the sheath 18 relative to the basket 10B and to retain the wires 11B in substantially the uniform orientation depicted in FIG. 7A. Alternatively, the portions of the distally extending loops of wires 11B can be secured together by solder, for example.

It will now be understood that surgical retrieval baskets, such as baskets 10, 10A, and 10B, according to this invention can be used as a substitute for similar prior art retrieval baskets such as those previously described. Further, this invention is applicable to retrieval baskets such as those disclosed in U.S. patent application Ser. No. 08/258,121 to Bates et al. (disclosing a basket having a plurality of sets of widely spaced wires with each set comprising a plurality of closely spaced filaments) for a Surgical Extractor and 08/ (Att. Doc. No. 94-137) to Leslie et al. filed on the same date as this application for a Surgical Extractor (disclosing a basket having a plurality of wires each having a single strand extending from a first end of the basket and a plurality of filaments extending from a second end of the basket). Both of these applications are assigned to the same assignee as this application and are incorporated by reference herein.

Therefore, each disclosed embodiment provides both a surgical extractor basket and a method for forming such baskets that meets the various objects of this invention. That is, this invention provides a method for producing wire retrieval baskets that have relatively consistent basket and wire characteristics by cold forming the basket wires prior to assembly of the enlarged basket portion. The method for producing such baskets according to this invention reduces the manual labor associated with baskets produced according to the prior art methods. Additionally, the ability to control many of the variables associated with producing surgical retrieval baskets according to this invention yields retrieval baskets that provide more consistent performance and reliability over prior art retrieval baskets. Thus this invention also meets the foregoing objects by providing a retrieval basket having cold worked, preformed wires, that are more reliable and consistent than prior art retrieval baskets and that can be selectively formed with arbitrary shapes, numbers of wires, and wire spacings.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A method for forming a surgical retrieval basket having a given number of wires formed in a predetermined configuration along a basket axis in an expanded state comprising the steps of:

(A) cold forming each of a plurality of axially extending, wires into the predetermined configuration;

(B) assembling the given number of wires with the predetermined configuration along the basket axis with the ends thereof being located together, said wires, in the assembled shape, conforming to the predetermined configuration of the basket in its expanded state; and (C) securing the ends of the assembled wires together thereby to form the basket.

2. A method for forming a surgical retrieval basket as recited in claim 1 wherein said cold forming step preforms a portion of each wire to extend radially from the basket axis between opposed ends thereof and said securing step secures opposed ends of the wires whereby the portions of the wires form the basket about the basket axis.

3. A method for forming a surgical retrieval basket as recited in claim 2 wherein each of the cold formed wires is rectangular in cross-section and lies in a plane between opposed ends of the basket whereby the wires after the securing step define a straight wire basket.

4. A method for forming a surgical retrieval basket as recited in claim 3 wherein the plurality of wires comprise an odd number.

5. A method for forming a surgical retrieval basket as recited in claim 3 wherein each of the wires has shape memory properties.

6. A method for forming a surgical retrieval basket as recited in claim 3 additionally comprising the step of heat treating each of the wires after being cold formed into the predetermined configuration and prior to said assembly step.

7. A method for forming a surgical retrieval basket as recited in claim 2 wherein the wires are cold formed in a helically extending fashion along an axis and the wires upon assembly define a helical basket with each of the wires comprising a turn in the helix.

8. A method for forming a surgical retrieval basket as recited in claim 7 wherein each of the wires has shape memory properties.

9. A method for forming a surgical retrieval basket as recited in claim 8 further comprising the step of heat treating the wires after said cold forming step and prior to said assembly step.

10. A method for forming a surgical retrieval basket as recited in claim 1 further comprising the step of heat treating each of said wires after said cold forming step and prior to said assembly step.

11. A method for forming a surgical retrieval basket as recited in claim 1 wherein each of the preformed wires extends in a loop fashion about an axis, the ends of each of the wires being substantially coextensive along the basket axis and said securing step secures the ends of each of said wires together.

12. A method for forming a surgical retrieval basket as recited in claim 11 wherein each of the wires is rectangular in cross-section and lies in a plane through the basket axis between the ends of the wires such that the sections of the wires define a straight wire basket.

13. A method for forming a surgical retrieval basket as recited in claim 12 wherein each of the wires has shape memory properties.

14. A method for forming a surgical retrieval basket as recited in claim 12 additionally comprising the step of heat treating each of the wires after said cold forming step and prior to said assembly step.

15. A method for forming a surgical retrieval basket having a given number of wires and, in an unrestrained expanded state, having a predetermined configuration, said method comprising the steps of:

preforming sections of each of a plurality of individual axially extending wires to the predetermined configuration wherein the characteristics of each of said wires is substantially identical, assembling from the plurality of wires the given number of wires with the ends thereof being located together whereby the given number of wires after assembly conform to the predetermined configuration of the basket in its expanded state, and securing the ends of the given number of wires together thereby to form the basket.

16. A method as recited in claim 15 wherein said preforming step comprises stamp pressing.

17. A method as recited in claim 15 wherein said preforming step comprises spring forming.

18. A method as recited in claim 15 wherein said preforming step preforms a portion of each of the wires to extend radially from the basket axis between opposite ends thereof and said securing step secures the opposed ends of the of the wires.

19. A method as recited in claim 18 wherein said preforming step processes wires having a rectangular cross-section to lie in a plane between opposed ends of the basket whereby the wires after said assembly and securing steps define a straight wire basket.

20. A method as recited in claim 18 wherein said preforming step forms each of the plurality of wires along a helical path with respect to the axis and the wires after said assembly and securing steps define a helical basket with each of the wire sections comprising a turn in the helix.

21. A method as recited in claim 18 wherein each of the wires is stainless steel.

22. A method as recited in claim 15 wherein each of the wires is stainless steel.

23. A method as recited in claim 15 wherein said preforming step forms each of the individual wires into a loop shape with opposed ends of the section proximate one another.

24. A method as recited in claim 15 further comprising the step of heat treating the preformed wires after said preforming step and prior to said assembly step.

25. A method as recited in claim 24 wherein said preforming step comprises stamp pressing.

26. A method as recited in claim 24 wherein said preforming step comprises spring forming.

27. A method as recited in claim 24 wherein said preforming step forms each of the plurality of wires into a loop shape with opposed ends of the section proximate one another.

* * * * *